US00PP34265P2

(12) United States Plant Patent
Knapp et al.

(10) Patent No.: US PP34,265 P2
(45) Date of Patent: May 24, 2022

(54) STRAWBERRY PLANT NAMED 'UCD MOJO'

(50) Latin Name: ***Fragaria* x *ananassa***
Varietal Denomination: UCD Mojo

(71) Applicant: The Regents of the University of California, Oakland, CA (US)

(72) Inventors: Steven J. Knapp, Davis, CA (US); Glenn S. Cole, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/160,298

(22) Filed: Jan. 27, 2021

(51) Int. Cl.
*A01H 5/08* (2018.01)
*A01H 6/74* (2018.01)

(52) U.S. Cl.
USPC ..... Plt./209

(58) Field of Classification Search
USPC ..... Plt./209, 208
CPC ... A01H 5/08; A01H 5/02; A01H 5/00; A01H 6/74; A01H 6/7409
See application file for complete search history.

(56) References Cited

U.S. PATENT DOCUMENTS

PP30,492 P3 * 5/2019 Hancock ..... A01H 6/7409 Plt./209

OTHER PUBLICATIONS

Bringhurst et al. Six new strawberry varieties released. California Agriculture 1980, 34: 12-15. (Year: 1980).*
Pincot et al. Social Network Analysis of the Genealogy of Strawberry: Retracing the Wild Roots of Heirloom and Modern Cultivars, Genealogy of Cultivated Strawberry, posted online 2020, retrieved from the Internet at https://www.biorxiv.org/content/10.1101/2020.09.30.320689v1.full.pdf, 31 pp. (Year: 2020).*
Test Agreement for Strawberries, 10 pp. 2016 Dec. 6, 2021.

* cited by examiner

*Primary Examiner* — June Hwu
(74) *Attorney, Agent, or Firm* — Kilpatrick Townsend & Stockton LLP

(57) ABSTRACT

'UCD Mojo' is an extreme day neutral cultivar of a strawberry plant adapted for summer-planting that provides high yields.

2 Drawing Sheets

Genus and species: The strawberry plant of this invention is botanically known as *Fragaria* x *ananassa* Duchesne.

Variety denomination: The variety denomination is 'UCD Mojo'.

BACKGROUND

The terms 'extreme day-neutral' (EDN) and 'summer-plant' are synonyms for photoperiod insensitive cultivars adapted for summer-plant production. EDN cultivars flower under short and long daylengths and are adapted for contra-season production. While many day neutral (DN) cultivars flower over the summer months, many do not perform well or produce high yields when planted at the height of summer. The specific factors that differentiate DN from EDN cultivars are unknown but appear to be genetically complex. Empirical testing (phenotyping in summer-plant production systems) was conducted on cultivars to identify summer-plant-adapted hybrids and to determine the genotype of hybrids for the PERPETUAL FLOWERING (PF) mutation, which enables flowering under long daylengths and is necessary for production in contra-season production systems, e.g., summer planting for fall production.

BRIEF SUMMARY

This invention relates to a new and distinct extreme day-neutral (or summer-plant) strawberry cultivar designated as 'UCD Mojo'. 'UCD Mojo' is adapted for contra-season and protected culture production in California and other parts of the world. 'UCD Mojo' originated from a cross that is believed to have occurred in the winter of 2012 between '07C203P001' (unpatented) and '08C150P009' (unpatented). It is unknown which plant is the female parent. The parent varieties were identified and the pedigree reconstructed using DNA forensic approaches involving exclusion analysis of DNA fingerprints of the strawberry germplasm collection of about 1,200 individual cultivars maintained by the applicant/assignee in Davis, Calif. Seeds of the cross were harvested from greenhouse-grown plants in the spring of 2012 and germinated in June 2012. Seedlings were transplanted to a greenhouse in July 2012 and transplanted to the field in October 2012. Daughter plants (clones) of 'UCD Mojo' were initially produced and harvested from the mother plant in 2013. 'UCD Mojo' has since been preserved by asexual propagation.

The plant of this selection was initially tested as '12C166P002' and later called 'EDN19' for evaluation in field trials.

'UCD Mojo' was initially selected based on the intensity of flowering under long day lengths and high summer temperatures in Winters, Calif. It was discovered using phenotypic analysis and genotyping with single nucleotide polymorphism (SNP) markers that 'UCD Mojo' is homozygous for the dominant allele of the PF mutation, which is a single dominant mutation that is necessary and sufficient for day-neutral flowering in descendants of a male wild ecotype *Fragaria virginiana* subsp. *glauca* plant that was collected in the Wasatch mountains in Utah (see, e.g., Bringhurst et al., *Calif. Agric.* 34: 12-15, 1980; Bringhurst et al., *Acta Hortic.* 265: 35-42, 1989). 'UCD Mojo' was determined to be well-adapted for summer-plant production.

Comparison variety 'UCD Finn' (U.S. Plant patent application Ser. No. 17/160,297, filed Jan. 27, 2021) is heterozygous for the PF mutation, as is comparison variety 'Portola' (U.S. Plant Pat. No. 20,552). Fruit of 'UCD Mojo' has higher sugar-to-acid ratios and is therefore sweeter than fruit from 'Portola'. 'UCD Mojo' is significantly more acidic than 'UCD Finn'. 'UCD Mojo' also has firmer fruit compared to 'Portola' and a fruit total soluble solids content that is significantly greater than that of 'Portola'. 'UCD Mojo' is later flowering than 'UCD Finn'. The fruit color of 'UCD Mojo' is more orange than that of 'Portola' and 'UCD Finn'.

'UCD Mojo' was genotyped with a 50,000-SNP array (Hardigan et. al., *Frontiers in Plant Science* 10:1789, 2020). After quality- and LD-pruning, 31,212 SNP markers with well-separated codominant genotypic clusters were selected for further analysis. The analyses confirmed that 'UCD Finn' is genetically distinct from parent varieties '07C203P001' and '08C150P009', 'UCD Finn', 'Portola', and over 500 additional varieties that were tested. 'UCD Mojo' is also shorter and a more spreading plant type than parent variety '07C203P001'. In addition, the fruit of 'UCD Finn' is long and conic compared to shorter, round conic fruit of '07C203P001. Stolon (runner) production for 'UCD Mojo' is less that than of parent '08C150P009'. 'UCD Mojo' is also more susceptible to Verticillium Wilt and more resistant to Macrophomina relative to parent '08C150P009'.

'UCD Mojo' is maintained by annual asexual propagation by stolons in Winters, Calif.

BRIEF DESCRIPTION OF THE DRAWINGS

The colors in the photograph are depicted as nearly true as is reasonably possible to obtain in color reproductions of this type.

DETAILED DESCRIPTION

Figure 1:
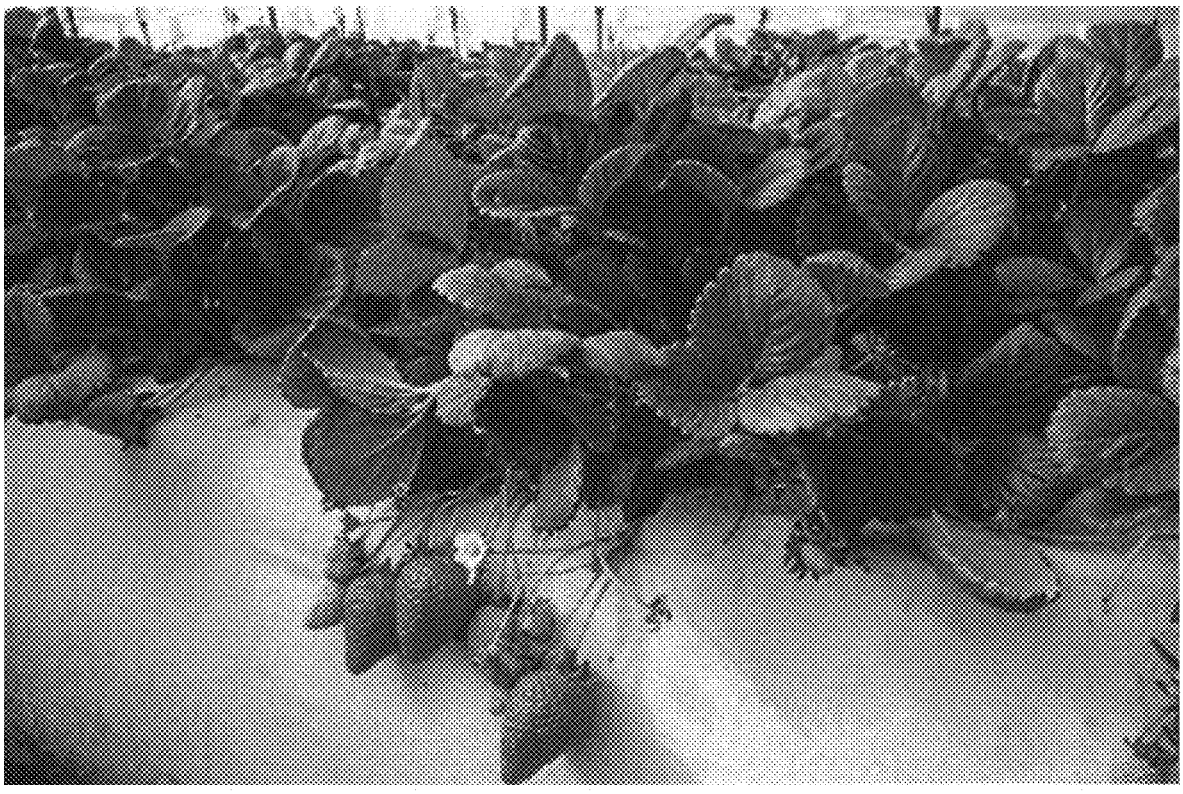
FIG. 1 depicts general plant and fruiting characteristics of 'UCD Mojo'.
Figure 2:
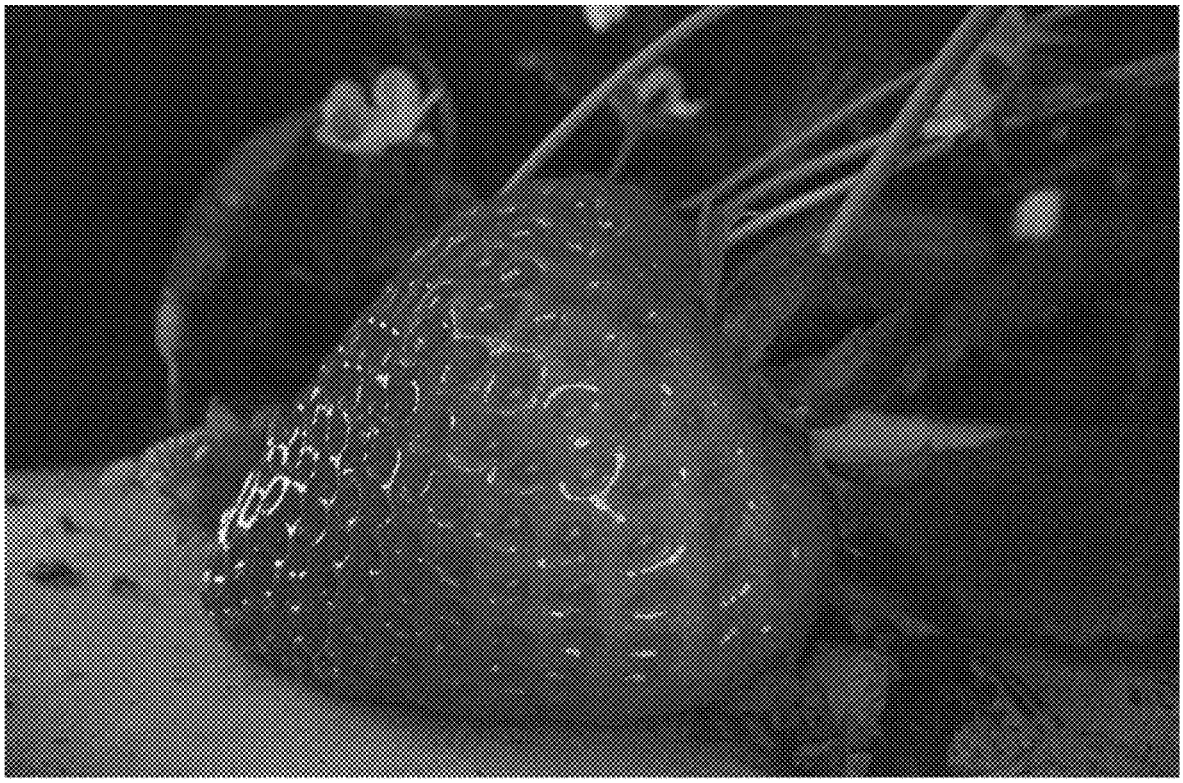
FIG. 2 shows a representative fruit of 'UCD Mojo'.

Based on field testing of day-neutral hybrids in 2016, 'UCD Mojo' was selected for advanced testing in replicated yield trials in 2017, 2018, and 2019. The 2017 and 2018 yield trials were performed in 24-plant (small) plots, whereas the 2019 yield trials were performed in 50-plant (large) plots. The most important observations and conclusions from these yield trials are enumerated below.

The cumulative marketable fruit yields of 'UCD Finn' and 'UCD Mojo' were comparable to those of 'Portola' in both conventional and organic production systems (Tables 1 and 2). We did not observe statistically significant differences in cumulative marketable fruit yields among cultivars within or among environments.

Yields for all cultivars were substantially lower in organic than conventional production systems (Tables 1 and 2). Yields for 'UCD Finn' and 'UCD Mojo' were greater than 'Portola' in large-plot conventional trials. The difference for 'UCD Mojo' was significant (p=0.005), whereas the difference for 'UCD Finn' was not (p=0.1)). The marketable fruit percentages of 'UCD Finn', 'UCD Mojo', and 'Portola' were not significantly different (Table 2).

TABLE 1

Cultivar Yield and Fruit Weight Least Square Means.

| | Small Plot | | | Large Plot (Conventional) | | Large Plot (Organic) | |
|---|---|---|---|---|---|---|---|
| Cultivar | Yield (kg/ha) | Fruit Weight (g/fruit) | Marketable Fruit (%) | Yield (kg/ha) | Fruit Weight (g/fruit) | Yield (kg/ha) | Fruit Weight (g/fruit) |
| UCD Finn | 49,540 | 22.4 | 84.1 | 43,354 | 24.8 | 15,906 | 19.0 |
| UCD Mojo | 45,342 | 24.1 | 77.2 | 45,137 | 26.8 | 12,281 | 19.6 |
| Portola | 53,202 | 23.5 | 81.1 | 42,084 | 25.4 | 19,599 | 21.2 |

Cultivars were grown in randomized complete blocks experiment designs with two replications/entry and multiple harvests/environment. Cultivars were grown in 24-plant (small) plots in Ventura, CA in 2017 and Oso Flaco, CA in 2017 and 2018, and 50-plant (large) plots in Guadalupe, Ventura, Oso Flaco, and Lompoc, CA in 2019. Least square means (LSMs) are shown for cultivars across small-plot or large-plot yield trial environments and for conventional and organic production systems in large-plot yield trials.

TABLE 2

Contrasts Among Cultivar Least-Square Means for Yield and Fruit Weight.

| | UCD Finn - Portola | | UCD Mojo - Portola | | UCD Finn - UCD Mojo | |
|---|---|---|---|---|---|---|
| Experiment & Trait | Estimate | p-value | Estimate | p-value | Estimate | p-value |
| Small Plot | | | | | | |
| Yield (kg/ha) | −3,662 | 0.9360 | −7,860 | 0.5011 | 4,198 | 0.9001 |
| Fruit Weight (g/fruit) | −1.2 | 0.0750 | 0.5 | 0.0578 | −1.7 | 0.0075 |
| Marketable Fruit (%) | 3.1 | 0.6989 | −3.8 | 0.5089 | 6.9 | 0.0781 |
| Large Plot (Conventional) | | | | | | |
| Yield (kg/ha) | 1,270 | 0.7631 | 3,053 | 0.1554 | −1,782 | 0.5422 |
| Fruit Weight (g/fruit) | −0.6 | 0.6346 | 1.4 | 0.1406 | −2.0 | 0.0224 |
| Large Plot (Organic) | | | | | | |
| Yield (kg/ha) | −3,693 | 0.1002 | −7,318 | 0.0051 | 3,626 | 0.1067 |
| Fruit Weight (g/fruit) | −2.2 | 0.1327 | −1.6 | 0.3294 | −0.6 | 0.8669 |

Cultivars were grown in randomized complete blocks experiment designs with two replications/entry and multiple harvests/environment. Cultivars were grown in small (24 plant) plots in Ventura, CA in 2017 and Oso Flaco, CA in 2017 and 2018, and large (50 plant) plots in Guadalupe, Ventura, and Oso Flaco, CA in 2019. Contrasts are shown for comparisons of UCD Finn and UCD Mojo to Portola and each other.

'UCD Finn' and 'UCD Mojo' were significantly sweeter than 'Portola' (Tables 3 and 4). When compared to 'Portola', mean Brix (°Bx) increase was 1.21 for 'UCD Finn' (p=0.0009) and 0.95 for 'UCD Mojo' (p=0.0106). The improved sweetness was a significant factor in the selection of 'UCD Finn' and 'UCD Mojo' for commercial advancement.

'UCD Finn' and 'UCD Mojo' were also significantly firmer than 'Portola' (Tables 3 and 4). When compared to 'Portola', the mean increase in fruit firmness was 52.3 g for 'UCD Finn' (p=0.0005) and 81.8 g for 'UCD Mojo' ($p \leq 0.0001$).

The titratable acid (TA) percentages of 'UCD Finn' and 'UCD Mojo' were not significantly different from 'Portola'; however, 'UCD Mojo' was significantly more acidic than 'UCD Finn' (Table 4).

The sugar-to-acid ratio (TSS/TA) was significantly greater for 'UCD Finn' than 'UCD Mojo' and 'Portola' (Table 4). The higher the ratio the greater the perceived sweetness; hence, 'UCD Finn' had greater perceived sweetness than 'UCD Mojo'. The sugar-to-acid ratios for 'UCD Mojo' and 'Portola' were not significantly different.

TABLE 3

Cultivar Least Square Means for Fruit Quality Traits.

| Cultivar | Firmness (g) | Degrees Brix (° Bx) Fresh | Degrees Brix (° Bx) Frozen | TA (%) | Sugar:Acid Ratio (° Bx/TA) |
|---|---|---|---|---|---|
| UCD Finn | 370 | 8.88 | 9.44 | 0.72 | 13.3 |
| UCD Mojo | 399 | 8.62 | 8.92 | 0.83 | 10.8 |
| Portola | 318 | 7.67 | 7.83 | 0.75 | 10.5 |

Cultivars were grown in randomized complete block experiment designs on five farms over two years (five year × location combinations) with two replications/entry, two harvests/environment, and one to three subsamples/harvest. Least square means were estimated for cultivars across locations and years. Fruit firmness (g of force) was measured on fresh fruit samples in the field using a handheld penetrometer with a 3 mm probe. Degrees Brix (° Bx) was measured on fresh fruit samples in the field using a handheld refractometer (Fresh) and previously frozen fruit samples in the laboratory using a benchtop refractometer (Frozen). Titratable acid (TA) percentages were measured on previously frozen fruit samples in the laboratory using a benchtop titrator.

TABLE 4

Contrasts Between Cultivar Least-Square Means for Fruit Quality Traits.

| Trait | UCD Finn – Portola Estimate | UCD Finn – Portola p-value | UCD Mojo – Portola Estimate | UCD Mojo – Portola p-value | UCD Finn – UCD Mojo Estimate | UCD Finn – UCD Mojo p-value |
|---|---|---|---|---|---|---|
| ° Bx Fresh | 1.21 | 0.0009 | 0.95 | 0.0106 | 0.26 | 0.8089 |
| ° Bx Frozen | 1.61 | 0.0008 | 1.09 | 0.0179 | 0.51 | 0.4060 |
| TA (%) | −0.04 | 0.6199 | 0.08 | 0.1158 | −0.11 | 0.0114 |
| ° Bx/TA | 2.77 | 0.0081 | 0.22 | 0.9894 | 2.55 | 0.0149 |
| Firmness (g) | 52.29 | 0.0005 | 81.78 | <0.0001 | −29.69 | 0.1102 |

Cultivars were grown in randomized complete blocks experiment designs on five farms over two years (five year × location combinations) with two replications/entry, two harvests/environment, and one to three subsamples/harvest.

The improved sweetness and firmness of 'UCD Finn' and 'UCD Mojo' persisted in postharvest storage (Tables 5-7). 'UCD Finn', 'UCD Mojo' were significantly sweeter and firmer than 'Portola' over 14 days in cold storage. As expected, fruit weight decreased for each cultivar over time in cold storage. The weight loss from desiccation was significantly greater for 'Portola' than 'UCD Finn' (Table 6). The fruit weight loss for 'UCD Mojo' was not significantly different from 'Portola' or 'UCD Finn'. We did not observe significant differences among cultivars for leakage or mold percentages.

TABLE 5

Cultivar Least Square Means for Postharvest Traits.

| Cultivar | Marketabihty | Firmness (g) | Degrees Brix (° Bx) | Fruit Weight (g) | Leakage (%) | Mold (%) |
|---|---|---|---|---|---|---|
| UCD Finn | 2.0 | 397 | 8.5 | 514 | 1.1 | 0.7 |

TABLE 5-continued

Cultivar Least Square Means for Postharvest Traits.

| Cultivar | Marketabihty | Firmness (g) | Degrees Brix (° Bx) | Fruit Weight (g) | Leakage (%) | Mold (%) |
|---|---|---|---|---|---|---|
| UCD Mojo | 2.2 | 414 | 8.3 | 527 | 0.0 | 0.9 |
| Portola | 2.1 | 325 | 7.5 | 535 | 0.4 | 0.7 |

Fruit were stored in standard 'one-pound' clamshells at 4° C. for 14 days. Traits were measured at 0, 7, and 14 days postharvest (DPH). The marketability of fruit was visually rated on a 1 to 5 scale, where 1 = excellent, 2 = good, 3 = fair, 4 = poor, and 5 = unacceptable. Fruit firmness (g) was measured on fresh fruit samples using a handheld penetrometer with a 3 mm probe. Degrees Brix was measured using a handheld refractometer. Fruit weight (g) was the weight of fruit stored in a standard 'one-pound' clamshell.

TABLE 6

Contrasts Between Least-Square Means for Postharvest Traits.

| Trait | UCD Finn - Portola Estimate | UCD Finn - Portola p-value | UCD Mojo - Portola Estimate | UCD Mojo - Portola p-value | UCD Finn - UCD Mojo Estimate | UCD Finn - UCD Mojo p-value |
|---|---|---|---|---|---|---|
| Marketability | −0.1 | 0.8129 | 0.1 | 0.9103 | −0.2 | 0.4171 |
| Firmness (g) | 72.1 | <0.0001 | 89.1 | <0.0001 | −17.0 | 0.5521 |
| Brix (° Bx) | 1.1 | <0.0001 | 0.8 | 0.0006 | 0.3 | 0.6718 |
| Fruit Weight (g) | −20.8 | 0.0033 | −8.1 | 0.4960 | −12.7 | 0.1274 |
| Leakage (%) | 0.7 | 0.7373 | −0.4 | 0.9460 | 1.1 | 0.4029 |
| Mold (%) | 0.0 | 1.0000 | 0.3 | 0.9795 | −0.3 | 0.9795 |

Fruit were stored in standard 'one-pound' clamshells at 4° C. for 14 days. Traits were measured at 0, 7, and 14 days postharvest (DPH). The marketability of fruit was visually rated on a 1 to 5 scale, where 1 = excellent, 2 = good, 3 = fair, 4 = poor, and 5 = unacceptable. Fruit firmness (g) was measured on fresh fruit samples using a handheld penetrometer with a 3 mm probe. Degrees Brix was measured using a handheld refractometer. Fruit weight (g) was the weight of fruit stored in a standard 'one-pound' clamshell. Contrasts were estimated as differences between cultivar least-square means (UCD Finn - Portola, UCD Mojo - Portola, and UCD Finn - UCD Mojo).

TABLE 7

Cultivar Least Square Means for Postharvest Traits.

| Trait | UCD Finn | UCD Mojo | Portola |
|---|---|---|---|
| 0 DPH | | | |
| Marketability | 1.0 | 1.2 | 1.0 |
| Firmness (g) | 359 | 396 | 305 |
| Brix (° Bx) | 9.0 | 8.4 | 7.4 |
| Fruit Weight (g) | 523 | 536 | 544 |
| Leakage (%) | 0.0 | 0.0 | 0.0 |
| Mold (%) | 0.0 | 0.0 | 0.0 |
| 7 DPH | | | |
| Marketability | 2.0 | 2.2 | 2.3 |
| Firmness (g) | 427 | 437 | 338 |
| Brix (° Bx) | 8.7 | 8.3 | 7.7 |
| Fruit Weight (g) | 515 | 527 | 535 |
| Leakage (%) | 0.0 | 0.0 | 0.0 |
| Mold (%) | 0.0 | 0.2 | 0.2 |
| 14 DPH | | | |
| Marketability | 3.1 | 3.3 | 3.2 |
| Firmness (g) | 406 | 409 | 331 |
| Brix (° Bx) | 8.0 | 8.3 | 7.3 |
| Fruit Weight (g) | 505 | 518 | 526 |
| Leakage (%) | 3.3 | 0.0 | 1.2 |
| Mold (%) | 2.0 | 2.7 | 1.8 |

Fruit were stored in standard 'one-pound' clamshells at 4° C. for 14 days. Traits were measured at 0, 7, and 14 days postharvest.

These cultivars were screened for resistance to *Fusarium* wilt, *Verticillium* wilt, and *Macrophomina* (Table 8). 'UCD Finn' and 'UCD Mojo' were susceptible to *Fusarium* wilt, whereas 'Portola' is resistant. 'UCD Mojo' was resistant to *Macrophomina*, whereas 'UCD Finn' and 'Portola' are susceptible. The three cultivars were moderately susceptible to *Verticillium* wilt and not significantly different.

TABLE 8

Resistance to Soilborne Diseases.

| | *Macrophomina* | *Fusarium wilt* | | *Verticillium wilt* | |
|---|---|---|---|---|---|
| Cultivar | 2016 | 2016 | 2017 | 2017 | 2018 |
| UCD Finn | 5.0a | 5.0a | 5.0a | 3.1a | 3.9a |
| UCD Mojo | 1.4b | 5.0a | 4.6a | 3.3a | 2.3a |
| Portola | 4.8a | 1.3b | 2.1b | 3.9a | 3.1a |

*Macrophomina*, *Fusarium wilt*, and *Verticillium wilt* resistance phenotypes for UCD Finn, UCD Mojo, and Portola. Plants were scored on a 1-5 ordinal scale, where 1 = resistant, 2 = moderately resistant, 3 = moderately susceptible, 4 = susceptible, and 5 = highly susceptible. Resistance phenotypes were recorded from field tests of artificially inoculated plants grown in fumigated soils at Armstrong Farm, Davis, CA. Least-square means (LSMs) were estimated from four replications per environment with plants grown in randomized complete blocks experiment designs. LSMs followed by the same letter are not significantly different.

Botanical description: The following botanical descriptors are characteristic of 'UCD Mojo'. The descriptors were collected from two different sites in October, 2020 in Santa Maria, Calif. Colors are designated with reference to The Royal Horticultural Society (R.H.S.) Colour Chart, Sixth Edition, 2015. The characteristics of 'UCD Mojo' may vary in detail, depending upon environmental factors and culture conditions.

*Growth habitat*.—Semi-upright Plant height average of 241 mm. Plant spread average of 462 mm.
*Density of foliage*.—Medium.
*Vigor*.—Medium.
*Position of inflorescence in relation to foliage*.—Same Level.
*Number of stolons*.—Medium.
*Stolon, anthocyanin coloration*.—Medium.
*Stolon, pubescence*.—Present, but sparse.
*Stolon, color*.—N144A.
*Leaf size*.—Medium.
*Leaf color*.—Adaxial 147A. Abaxial 147B.
*Leaf blistering*.—Medium.
*Leaf glossiness*.—Medium.
*Leaf variegation*.—Absent.
*Mid-tier (from middle of the plant), terminal leaflet, length*.—Average of 68 mm.
*Mid-tier (from middle of the plant), terminal leaflet width*.—Average of 104 mm.
*Terminal leaflet, shape of base*.—Obtuse.
*Terminal leaflet, margin*.—Serrate to crenate.
*Terminal leaflet, shape in cross section*.—Convex.
*Petiole, length*.—Average of 143 mm.
*Petiole, attitude of hairs*.—Horizontal.
*Petiole, color*.—144C.
*Stipule, core color*.—145C.
*Stipule, margin color*.—146C.
*Pedicel, attitude of hairs*.—Slightly outwards.
*Pedical, color*.—144C.
*Flower, arrangement of petals*.—Touching.
*Flower, petal number*.—Average of 6.
*Flower, petal length*.—Average of 9.1 mm.
*Flower, petal width*.—Average of 9.0 mm.
*Flower, petal, color of upper side*.—NN155C.
*Flower, petal, color of lower side*.—NN155C.
*Flower, calyx diameter*.—Average of 27 mm.
*Flower, color of calyx*.—147A.
*Flower, corolla diameter*.—Average of 20 mm.
*Flower, number of sepals per flower*.—Average of 11.
*Flower, stamen number*.—Average of 27.
*Fruit, achene color*.—11A.
*Fruit, position of achenes*.—Below surface.
*Fruit, length*.—Average of 49 mm.
*Fruit, width*.—Average of 41 mm.
*Fruit, extent/size of hollow core*.—Average of 8.9 mm.
*Fruit size*.—Average of 31 grams/per fruit.
*Fruit shape*.—Conical.
*Fruit, difference in shape of terminal and other fruits*.—None or very slight.
*Fruit, exterior color*.—45A.
*Fruit, flesh color*.—40B.
*Fruit, core color*.—35A.
*Fruit, evenness of color*.—Even or very slightly uneven.
*Fruit glossiness*.—Medium.
*Fruit, evenness of surface*.—Even or very slightly uneven.
*Fruit, width of band without achenes*.—Absent or very narrow.
*Fruit, position of calyx attachment*.—Level with fruit.
*Fruit, attitude of sepals*.—Outwards.
*Fruit, diameter of calyx in relation to fruit diameter*.—Slightly smaller.
*Fruit, adherence of calyx*.—Weak.
*Fruit firmness*.—Firm.
*Time of beginning of flowering*.—Early.
*Time of beginning of fruit ripening*.—Early.
*Type of bearing*.—Extreme day neutral.

What is claimed is:

1. A new and distinct cultivar of strawberry plant named 'UCD Mojo', substantially as described and illustrated herein.

* * * * *